United States Patent [19]
Belmore et al.

[11] Patent Number: 5,141,314
[45] Date of Patent: Aug. 25, 1992

[54] SPECTROANALYTICAL SYSTEM

[75] Inventors: Richard J. Belmore, Bridgewater; John A. Bernier, Lexington, both of Mass.

[73] Assignee: Thermo Jarrell Ash Corporation, Waltham, Mass.

[21] Appl. No.: 662,924

[22] Filed: Mar. 1, 1991

[51] Int. Cl.⁵ .................... G01J 3/443; G01N 21/67
[52] U.S. Cl. .................................................. 356/313
[58] Field of Search .................... 356/307, 306, 313

[56] References Cited

U.S. PATENT DOCUMENTS

| | | | |
|---|---|---|---|
| 2,744,438 | 5/1956 | Steinhaus et al. | 356/313 |
| 3,655,987 | 4/1972 | Hinds. | |
| 3,689,770 | 9/1972 | Dion. | |
| 3,999,061 | 12/1976 | McLaughlin. | |
| 4,348,110 | 9/1982 | Ito. | |
| 4,393,327 | 7/1983 | Walters et al. | 356/313 |
| 4,518,443 | 6/1970 | Engelmann. | |
| 4,645,342 | 2/1987 | Tanimoto et al. | 356/307 |
| 4,661,693 | 4/1987 | Masanobu. | |
| 4,723,438 | 2/1988 | Adler-Golden et al. | 356/313 |

OTHER PUBLICATIONS

CEC Bulletin 22101, Direct Reading Emission Spectrometers, May 1965.
Zynger et al., *Applied Spectroscopy*, vol. 29, No. 3 May/-Jun. 1975, pp. 244-255.
Matsumoto, *Determination of C, P and S in Steels by Time-resolved Atomic Emission Spectrometry* (1990).

*Primary Examiner*—F. L. Evans
*Attorney, Agent, or Firm*—Fish & Richardson

[57] ABSTRACT

A spectroanalytical system with radiation dispersing apparatus having structure for dispersing radiation into a spectrum for concurrent application to a plurality of exit ports; a plurality of radiation sensor channel circuits, each circuit being optically coupled to a corresponding exit port for monitoring radiation at that exit port; sample excitation apparatus for exciting sample material to be analyzed to spectroemissive levels for generating a beam of radiation for dispersion by the dispersion structure; and controller structure for triggering the excitation apparatus to excite the sample material and for generating a gating interval by the channel circuitry for accumulating radiation data during an interval that commences subsequent to application of maximum energy to the sample by the excitation apparatus.

25 Claims, 2 Drawing Sheets

SPECTROANALYTICAL SYSTEM

BACKGROUND AND SUMMARY OF THE INVENTION

This invention relates to spectroscopic analysis and more particularly to spectroanalytical systems of the polychromator type.

In spectroscopic analytical techniques using emission sources such as a high voltage spark source or an arc source, material from the sample to be analyzed is introduced into an analytical region and excited to spectroemissive levels sufficient to emit detectable radiation characteristic of elements in the sample. Excitation may be by a spark or arc discharge or by plasma, alone or with supplemental excitation, or otherwise. The resulting emitted radiation typically is dispersed and analyzed spectroscopically to quantitatively determine elemental compositions of sample materials. Such techniques are useful in analyzing metals and metal alloys, for example.

In accordance with one aspect of the invention, there is provided a spectroanalytical system with radiation dispersing apparatus having dispersing structure for dispersing radiation into a spectrum for concurrent application to an exit port; a radiation sensor channel circuit that is optically coupled to the exit port for monitoring radiation at that exit port; sample excitation apparatus for exciting sample material to be analyzed to spectroemissive levels for generating a beam of radiation for dispersion by the dispersing structure; and controller structure for triggering the excitation apparatus to excite the sample material and for generating a gating interval by the channel circuitry for accumulating radiation data during an interval that commences subsequent to application of maximum energy to the sample by the excitation apparatus.

In preferred embodiments, the radiation dispersing apparatus includes polychromator apparatus with entrance slit structure, exit slit structure composed of a series of exit slit elements disposed along a Rowland circle, each exit slit element defining an exit port, and the dispersing structure is disposed between the entrance and said exit slit structures. The controller structure times the gating interval from the excitation triggering and initiates the gating interval at least thirty microseconds subsequent to application of maximum energy to the sample by the excitation apparatus.

In a particular embodiment, the excitation apparatus includes arc stand structure with counter electrode structure for applying an electric discharge to sample material to be analyzed; a trigger gap connected to the counter electrode through a spark modification circuit, and the controller structure includes means for generating a control signal to fire the trigger gap, the sample excitation apparatus being adapted to generate an electrical discharge with a maximum amplitude of at least ten amperes and a duration of less than one millisecond for application to sample material to be analyzed. An input control is connected to the controller structure and the controller structure includes a gate start register and a gate interval register, each of which is a multi-bit register that is set by signals from the input control for controlling the start and duration of the gating interval. The sample excitation apparatus includes charging circuitry, discharge circuitry, a low voltage capacitor connected between the charging and discharging circuitry and switchable between different capacitor values; a resistor switchable between different resistance values; and an inductance switchable between different inductance values, the resistor and inductance being connected to the discharge circuitry. Each channel circuit includes a photomultiplier tube that produces an output current as a function of radiation passing through its exit port, an operational amplifier for transforming the output current to a voltage, an integrator that has a capacitor in its feedback path, a first switch responsive to a signal from the controller for applying the voltage from the operational amplifier to the integrator so that when the first switch is closed, the output voltage of the integrator is proportional to the integral of the photomultiplier current, a storage register, an analog to digital converter connected to the storage register, and a second switch responsive to a signal from the controller for connecting the output of the integrator to the analog to digital converter for conversion of the value stored in the integrator to digital form for application to the storage register.

In accordance with another aspect of the invention, there is provided a method of spectroanalysis comprising the steps of exciting sample material to be analyzed to spectroemissive levels with excitation apparatus to generate a beam of radiation; dispersing the beam of radiation into a spectrum for concurrent application to a plurality of exit ports; monitoring radiation at each exit port with channel circuitry corresponding to each exit port; triggering the excitation apparatus to excite the sample material; and generating a gating interval that commences subsequent to application of maximum energy to the sample material by the excitation apparatus for accumulating data on radiation monitored by the channel circuitry during the gating interval. Preferably, the method includes the steps of generating a first signal to trigger the excitation apparatus and a second signal times and coordinated with the first signal to initiate the gating interval at least thirty microseconds subsequent to application of maximum energy to the sample by the excitation apparatus.

In accordance with another aspect of the invention, there is provided a spectroanalytical system with radiation dispersing apparatus for dispersing radiation into a spectrum for concurrent application to a plurality of exit ports; a plurality of radiation sensor channel circuits, each circuit being optically coupled to a corresponding exit port for monitoring radiation at that exit port; sample excitation apparatus for exciting sample material to be analyzed to spectroemissive levels for generating a beam of radiation for dispersion by the dispersing structure, the excitation apparatus including arc stand structure with counter electrode structure for applying an electric discharge to sample material to be analyzed, a trigger gap connected to the counter electrode through a spark modification circuit, and the controller structure includes means for generating a control signal to fire the trigger gap, the sample excitation apparatus being adapted to generate an electrical discharge with a maximum amplitude of at least ten amperes and a duration of less than one millisecond for application to sample material to be analyzed. Preferably, the sample excitation apparatus includes charging circuitry, discharging circuitry, a low voltage capacitor connected between the charging and discharging circuitry and switchable between different capacitor values; a resistor switchable between different resistance values; and an inductance switchable between different inductance values, the resistor and inductance being connected between the discharging circuitry and the counter electrode.

In accordance with another aspect of the invention, there is provided a spectroanalytical system with radiation dispersing apparatus for dispersing radiation into a spectrum for concurrent application to a plurality of exit ports; a plurality of radiation sensor channel circuits; sample excitation apparatus for exciting sample material to be analyzed to spectroemissive levels for generating a beam of radiation for dispersion by the dispersing apparatus; and controller structure for triggering the excitation apparatus to excite the sample material and for generating a gating interval by the channel circuits for accumulating data on the dispersed radiation. Each channel circuit is optically coupled to a corresponding exit port for monitoring radiation at that exit port. An input control is connected to the controller structure and the controller structure includes a gate start register and a gate interval register, each of which is a multi-bit register that is set by signals from the input control for controlling the start and duration of the gating interval. Preferably, each channel circuit includes a photomultiplier tube that produces an output current as a function of radiation passing through its exit port, an operational amplifier for transforming the output current to a voltage, an integrator that has a capacitor in its feedback path, a first switch responsive to a signal from the controller for applying the voltage from the operational amplifier to the integrator so that when the first switch is closed, the output voltage of the integrator is proportional to the integral of the photomultiplier current, a storage register, an analog to digital converter connected to the storage register, and a second switch responsive to a signal from the controller for connecting the output of the integrator to the analog to digital converter for conversion of the value stored in the integrator to digital form for application to the storage register.

Other features and advantages of the invention will be seen as the following description of a particular embodiment progresses, in conjunction with the drawings, in which.

Figure 1:
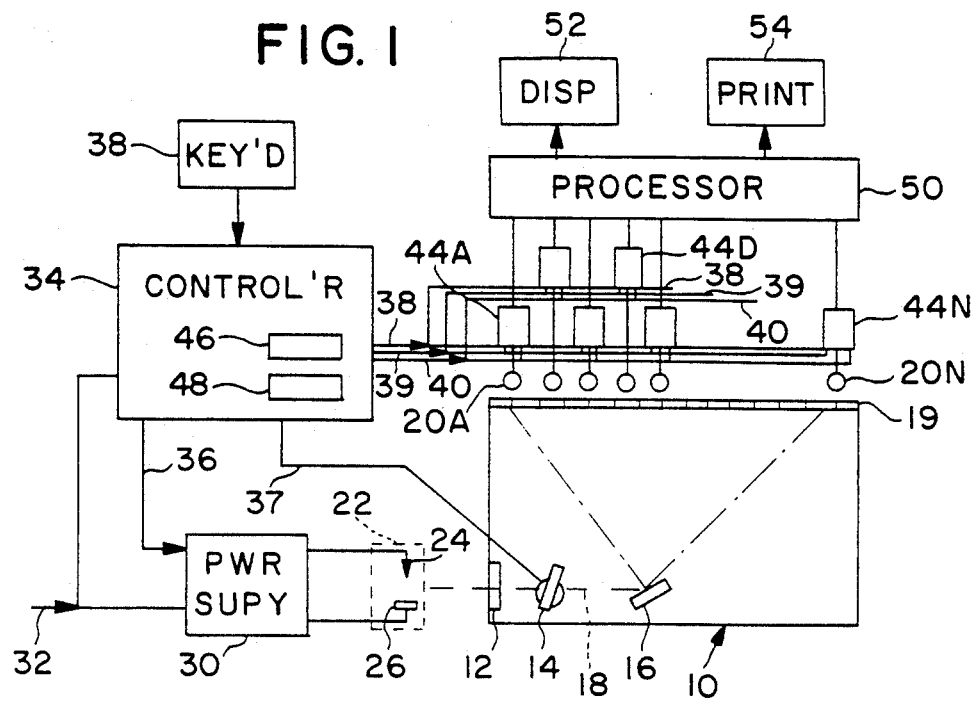
FIG. 1 is a diagram of a spectroanalytical system in accordance with the invention.
Figure 2:
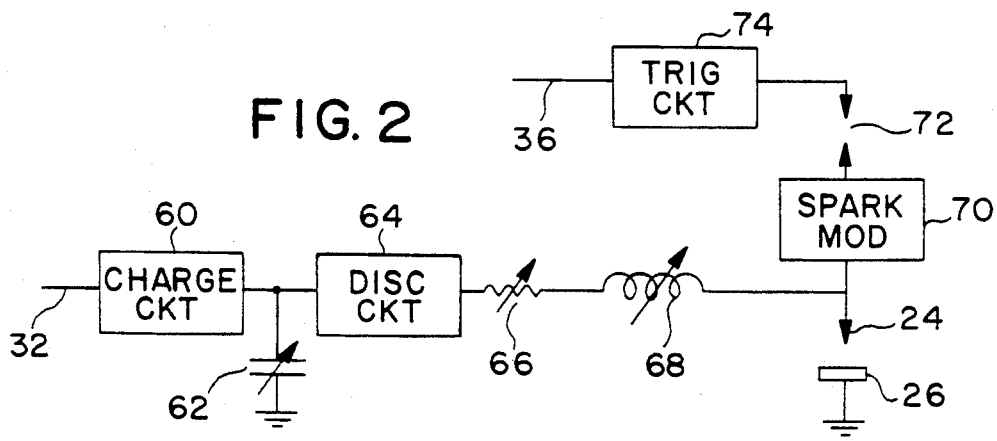
FIG. 2 is a diagram of the power supply control circuitry employed in the system shown in FIG. 1.
Figure 4:
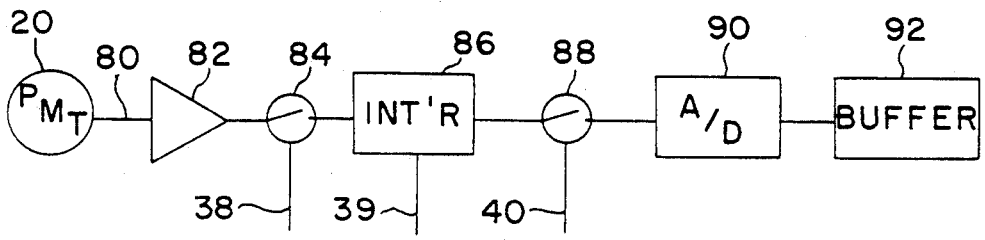
Figure 3A:
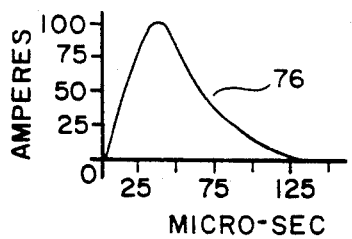
Figure 3B:
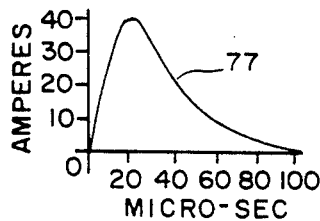
Figure 3C:
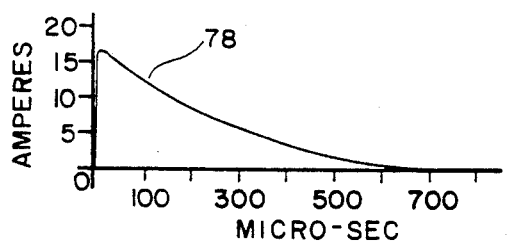
Figure 5A:
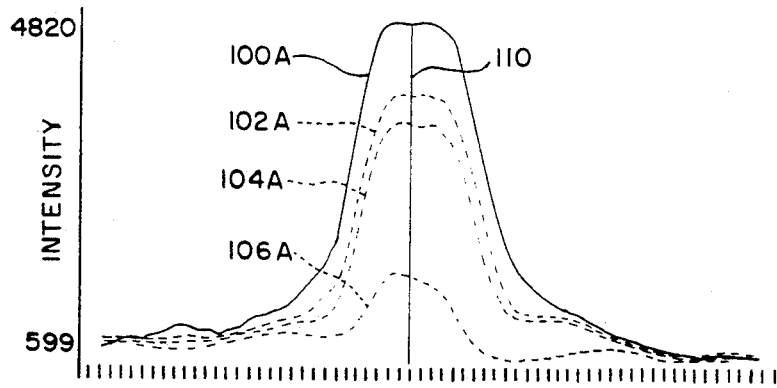
Figure 5B:
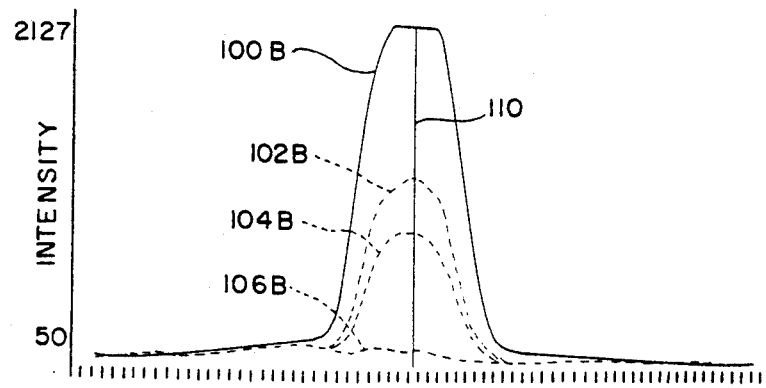

FIGS. 3a-c are a set of diagrams indicating waveform configurations produced by the power supply control circuitry shown in FIG. 2;

FIG. 4 is a diagram of channel readout circuitry employed in the system shown in FIG. 1; and FIGS. 5A and 5B are plots of data obtained with the system shown in FIG. 1, FIG. 5A being a graph of data accumulation on four different materials without gating control and FIG. 5B being a graph of data accumulation on the same four materials with gating control.

DESCRIPTION OF PARTICULAR EMBODIMENT

With reference to FIG. 1, the spectroanalytical system there diagrammatically illustrated includes polychromator 10 with entrance slit structure 12, spectrum shifter structure 14 and reflection grating 16 for dispersing incident radiation on beam axis 18 into a spectrum for sensing of a selected array of up to thirty-one photomultiplier tube sensors out of a group of up to sixty-three photomultiplier tube sensors 20A-N disposed along a Rowland circle at a radius of curvature of 0.75 meter. Disposed in front of entrance slit 12 is arc stand 22 (filled, for example, with argon) which includes counter electrode 24 and a grounded sample 26 to be analyzed. Power supply 30 operates the arc stand 22 in a flush, preburn and exposure cycle of variable duration to analyze sample material that is excited in the discharge between counter electrode 24 and sample 26. Power supply 30 is resynchronized with the 50 hertz or 60 hertz frequency on power line 32 every 0.1 second and receives trigger signals from controller 34 over line 36.

Associated with controller 34 is input keyboard control 38 which specifies spectroanalytical system operating mode and duration and operates in conjunction with controller 34 to provide output signals on line 36 to control power supply 30, signals on line 37 to control the spectrum shifter 14, and signals on lines 38–40 to control channel readout circuits 44A–N that are connected to corresponding photomultiplier tubes 20. Controller 34 includes gate start register 46 and gate interval register 48, each of which is an eight-bit register that is set by signals from input keyboard 38 to specify a time interval that is variable from 0–1155 microseconds in five microsecond increments. Coupled to the outputs of readout circuits 44 is data processor 50 for processing information generated from photomultiplier tubes 20 for application to output devices such as display 52 and printer 54.

Further details of power supply 30 may be seen with reference to FIG. 2. That circuitry includes charging circuit 60, low voltage capacitor 62 that is switchable between two microfarads and twelve microfarads value; discharge circuit 64; variable resistor 66 that is switchable between 3.3 ohms and 23.3 ohms; and variable inductance 68 that is switchable between 65 microhenries and 138 microhenries and is connected to counter electrode 24 of arc stand 22. Also connected to counter electrode 24 through spark modification circuit 70 is trigger gap 72 that is fired by trigger circuit 74 in response to control signals from controller 34 over line 36.

Discharge current waveforms that are applied to arc stand 22 by power supply 30 to produce sparks are indicated in FIG. 3. The indicated current flow of each discharge 76–78 commences about forty microseconds after the trigger signal on line 36 is applied to trigger circuit 74. In a high power mode (FIG. 3A), capacitor 62 has a value of twelve microfarads, resistor 66 has a value of 3.3 ohms, and inductor 68 has a value of 65 microhenries, the circuitry producing a pulse 76 of configuration shown in FIG. 3A with a maximum amplitude of about one hundred amperes at about thirty microseconds after the start of current flow (about seventy microseconds after the trigger pulse on line 36) and a duration of about 125 microseconds. In a medium power mode, capacitor 62 has a value of two microfarads, resistor 66 has a value of 3.3 ohms, and inductor 68 has a value of 138 microhenries, the circuitry producing a pulse 77 of configuration indicated in FIG. 3B with a maximum amplitude 108 of about forty amperes at about twenty microseconds after start of current flow (about sixty microseconds after the trigger pulse on line 36) and a duration of about one hundred microseconds. In a low power mode, capacitor 62 has a value of twelve microfarads, resistor 66 has a value of 23.3 ohms, and inductor 68 has a value of 138 microhenries, and produces an output pulse 78 of shape generally indicated in FIG. 3C with a maximum amplitude of about sixteen amperes at about thirty microseconds after start of current flow (about sixty microseconds after the trigger pulse on line 36) amperes and a duration of about 800 microseconds.

The triggering signal on line 36 from controller 34 may be repeated at a 180 hertz repetition rate or a 360 hertz repetition rate as selected by input control 38. Each spark at arc stand 22 produces thermal excitation of the sample material 26 and the resulting radiation is passed along beam path 18 through entrance slit 12 and spectrum shifter 14 to grating 16 for dispersion into a spectrum for sensing by the photomultiplier tubes 20 mounted at the corresponding exit slits 19 of the polychromator 10.

A diagram of each channel readout circuit 44 is shown in FIG. 4. The output current of nine stage photomultiplier tube 20 on line 80 is transformed to a voltage by operational amplifier 82 and applied to FET switch 84 which receives a control signal on line 38 from controller 34 for application to integrator 86 that has a capacitor in its feedback path so that when FET switch 84 is closed, the output voltage of integrator 86 is proportional to the integral of the photomultiplier current input. When switch 84 is open, the DC output voltage of integrator 86 is held at its present value. In response to a connect signal on line 40, FET switch 88 is closed to connect the output of integrator 86 to twelve bit analog to digital converter 90 for conversion of the value stored in integrator 86 to digital form for application to a buffer register 92 in processor 50. A signal from controller 34 on line 39 then zeros and clears integrator 86 for the next spark cycle.

The system, in a typical analytical sequence, performs a flush cycle of 3-7 seconds duration in which argon or a similar gas is flowed through the analytical gap in arc stand 22; a preburn cycle of the sample 26 to be analyzed of 1-100 seconds at a high (one hundred amperes) or medium (forty amperes) current; and an exposure interval of variable duration. In a typical spectrum shifter exposure interval of the type illustrated in FIG. 5, sixty-three data points are taken at a rate of about two data points per second, and the sample being analyzed is subjected to 180 spark discharges at each data point. Each data point, as indicated on the abscissa of FIG. 5, is offset by movement of spectrum shifter 14 about 0.06 angstrom from the adjacent data point. Thus, spectrum shifter 14 is shifted between data points to provide an incremental analytical scan of the type illustrated in FIG. 5 over a wavelength range of about four angstroms.

FIGS. 5A and 5B are plots of analytical data generated with sparks of medium power (FIG. 3B) of the carbon spectral line at 1930.93 A of four different sample materials, curves 100A and 100B representing output data on a sample of cast iron that has a carbon content of about 3.45 percent; curves 102A and 102B representing output data on a sample of low alloy stainless steel with about one percent carbon content; curves 104A and 104B representing output data on a sample of a low alloy steel with about 0.6 percent carbon content; and curves 106A and 106B representing output data on a sample of steel with a trace amount (about 0.006 percent) of carbon. The data of FIG. 5A were generated without gating control (that is, photomultiplier output data were integrated over each spark discharge cycle in conventional manner), and the curves of FIG. 5B were generated with gating control. The start of the FIG. 3B medium power spark pulse occurred about forty microseconds after the trigger pulse on line 36; the peak of the spark pulse occurs about sixty microseconds after the trigger pulse on line 36; the gating signal on line 38 to close FET switch 84 was generated from register 46 one hundred twenty microseconds after the trigger pulse on line 36 to power supply 30 (when the spark current was about five amperes); and FET switch 84 was opened (under control of register 48) two hundred microseconds after the trigger pulse on line 36 such that the gated integration intervals for collection of the data of FIG. 5B commenced at point 108 (about sixty microseconds after the amperage peak 110 of spark 77—FIG. 3B) when the spark current was about five amperes and decreasing, and had a duration of eighty microseconds each. The data measurements of FIG. 5A provided a background level value of about 600 units, a peak intensity of curve 100A of 4820 units; a peak intensity of curve 102A of 3949 units; a peak intensity of curve 104A of 3600 units; and a peak of curve 106A of 1684 units. As indicated in FIG. 5B, with gating control, the background level value was reduced to about 50 units; the peak of curve 100B was 2127 units; the peak of curve 102B was 1224 units; the peak of curve 104B was 854 units; and the peak of curve 106B (offset from carbon line 112) was 144 units.

It will be seen that system operation as indicated in FIG. 5B with gating control provides enhanced dynamic range.

While a particular embodiment of the invention has been shown and described, various modifications will be apparent to those skilled in the art, and therefore, it is not intended that the invention be limited to the disclosed embodiment, or to details thereof, and departures may be made therefrom within the spirit and scope of the invention.

What is claimed is:

1. A spectroanalytical system comprising
radiation dispersing apparatus having dispersing structure for dispersing radiation into a spectrum for application to an exit port;
a radiation sensor channel circuit, said circuit being optically coupled for monitoring radiation at said exit port;
sample excitation apparatus for exciting sample material to be analyzed to spectroemissive levels for generating a beam of radiation for dispersing by said dispersing structure, said sample excitation apparatus including circuitry for generating an electrical discharge with a maximum amplitude of at least ten amperes and of decreasing magnitude after said maximum amplitude, for application to sample material to be analyzed; and
controller structure for triggering said excitation apparatus to excite the sample material and for generating a gating interval by said channel circuit independent of said electrical discharge for accumulating radiation data during an interval that commences subsequent to application of maximum energy to said sample by said excitation apparatus.

2. The system of claim 1 wherein said radiation dispersing apparatus includes polychromator apparatus having entrance slit structure, exit slit structure composed of a series of exit slit elements disposed along a Rowland circle, each said exit slit element defining an exit port, and said dispersing structure is disposed between said entrance slit structure and said exit slit structure.

3. The system of claim 1 wherein said excitation apparatus includes arc stand structure that includes counter electrode structure for applying an electric discharge to sample material to be analyzed.

4. The system of claim 3 wherein said excitation apparatus includes a trigger gap connected to said counter electrode through a spark modification circuit, and said controller structure includes means for generating a control signal to fire said trigger gap.

5. The system of claim 1 wherein said electrical discharge has a duration of less than one millisecond.

6. The system of claim 1 wherein said controller structure times the initiation of said gating interval from the generation of a signal to trigger said excitation apparatus and initiates said gating interval at least thirty microseconds subsequent to application of maximum energy to said sample material by said excitation apparatus.

7. The system of claim 1 and further including an input control connected to said controller structure and wherein said controller structure includes a gate start register and a gate interval register, each of which is a multi-bit register that is set by signals from said input control for controlling the start and duration of said gating interval.

8. The system of claim 1 wherein said sample excitation apparatus includes charging circuitry, discharging circuitry, a low voltage capacitor connected between said charging and discharging circuitry and switchable between different capacitor values; a resistor switchable between different resistance values; and an inductance switchable between difference inductance values, said resistor and inductance being connected to said discharge circuitry.

9. The system of claim 1 wherein said channel circuit includes a photomultiplier tube that produces an output current as a function of radiation passing through said exit port, an operational amplifier for transforming said output current to a voltage, an integrator that has a capacitor in its feedback path, a first switch responsive to a signal from said controller structure for applying the voltage from said operational amplifier to said integrator so that when said first switch is closed, the output voltage of said integrator is proportional to the integral of the photomultiplier current.

10. The system of claim 9 wherein said channel circuit further includes a storage register, an analog to digital converter connected to said storage register, and a second switch responsive to a signal from said controller structure for connecting the output of said integrator to said analog to digital converter for conversion of the value stored in said integrator to digital form for application to said storage register.

11. A spectroanalytical system comprising
radiation dispersing apparatus having dispersing structure for dispersing radiation into a spectrum for concurrent application to a plurality of exit ports;
a plurality of radiation sensor channel circuits, each said circuit being optically coupled to a corresponding exit port for monitoring radiation at that exit port;
sample excitation apparatus for exciting sample material to be analyzed to spectroemissive levels for generating a beam of radiation for dispersion by said dispersing structure, said excitation apparatus including arc stand structure that includes counter electrode structure for applying an electric discharge that has a maximum amplitude of at least ten amperes an is of decreasing magnitude after said maximum amplitude to sample material to be analyzed, and a trigger gap connected to said counter electrode through a spark modification circuit; and
controller structure including means for generating a control signal to fire said trigger gap to excite the ample material and for generating a gating interval by said channel circuits independent of said electrical discharge for accumulating radiation data during an interval that commences subsequent to firing of said trigger gap.

12. The system of claim 11 wherein said radiation dispersing apparatus includes polychromator apparatus having entrance slit structure, exit slit structure composed of a series of exit slit elements disposed along a Rowland circle, each said exit slit element defining an exit port, and said dispersing structure is disposed between said entrance slit structure and said exit slit structure.

13. The system of claim 12 wherein said electrical discharge has a duration of less than one millisecond.

14. The system of claim 13 wherein said controller structure times the initiation of said gating interval from the generation of the signal to fire said trigger gap and initiates said gating interval at least thirty microseconds subsequent to application of maximum energy to said sample material by said excitation apparatus.

15. The system of claim 14 wherein said sample excitation apparatus includes charging circuitry, discharging circuitry, a low voltage capacitor connected between said charging and discharging circuities and switchable between different capacitor values; a resistor switchable between different resistance values; and an inductance switchable between different inductance values, said resistor and inductance being connected between said discharging circuitry and said counter electrode structure.

16. A spectroanalytical system comprising
radiation dispersing apparatus having dispersing structure for dispersing radiation into a spectrum for concurrent application to a plurality of exit ports;
a plurality of radiation sensor channel circuits, each said circuit being optically coupled to a corresponding exit port for monitoring radiation at that exit port;
sample excitation apparatus for exciting sample material to be analyzed to spectroemissive levels for generating a beam of radiation for dispersion by said dispersing structure, said sample excitation apparatus including circuitry for generating an electrical discharge with a maximum amplitude of at least ten amperes and of continuously decreasing magnitude after said maximum amplitude, for application to sample material to be analyzed; and
controller structure for triggering said excitation apparatus to excite the sample material and for generating a gating interval by said channel circuits independent of said electrical discharge for accumulating radiation data, each said channel circuit including a photomultiplier tube that produces and output current as a function of radiation passing through its exit port, an operational amplifier for transforming said output current to a voltage, an integrator that has a capacitor in its feedback path, and a first switch responsive to a signal from said controller structure for applying the voltage from said operational amplifier to said integrator so that when said first switch is closed, the output voltage of said integrator is proportional to the integral of the photomultiplier current.

17. The system of claim 16 and further including an input control connected to said controller structure and wherein said controller structure includes a gate start register and a gate interval register, each of which is a multi-bit register that is set by signals from said input control for controlling the start and duration of said gating interval.

18. The system of claim 17 wherein said controller structure times the initiation of said gating interval from the generation of the signal to trigger said excitation apparatus and initiates said gating interval at least thirty microseconds subsequent to application of maximum energy to said sample material by said excitation apparatus.

19. The system of claim 18 wherein said sample excitation apparatus includes charging circuitry, discharging circuitry, a low voltage capacitor connected between said charging and discharging circuitry and switchable between different capacitor values; a resistor switchable between different resistance values; and an inductance switchable between different inductance values, said resistor and inductance being connected to said discharge circuitry.

20. The system of claim 19 wherein each said channel circuit further includes a storage register, an analog to digital converter connected to said storage register, and a second switch responsive to a signal from said controller structure for connecting the outer of said integrator to said analog to digital converter for conversion of the value stored in said integrator to digital form for application to said storage register.

21. A spectroanalytical system comprising
polychromator apparatus having entrance slit structure, exit slit structure composed of a series of exit slit elements disposed along a Rowland circle, and dispersing structure disposed between said entrance slit structure and said exit slit structure for dispersing radiation passing through said entrance slit structure into a spectrum for concurrent application to the several exit slit elements of said exit slit structure;
radiation sensor channel circuitry optically coupled to each said exit slit element for monitoring radiation at that exit slit element;
sample excitation apparatus for exciting sample material to be analyzed to spectroemissive levels for passing a beam of radiation through said entrance slit structure for dispersion by said dispersing structure, said sample excitation apparatus including circuitry for generating an electrical discharge with a maximum amplitude of at least ten amperes and of continuously decreasing magnitude after said maximum amplitude for application to sample material t be analyzed; and
controller structure for triggering said excitation apparatus to excite the sample material and for generating a gating interval of less than one millisecond duration by said channel circuitry independent of said electrical discharge for accumulating radiation data during an interval that commences subsequent to application of maximum energy to said sample by said excitation apparatus.

22. The system of claim 21 wherein said excitation apparatus includes arc stand structure that includes counter electrode structure for applying an electric discharge to sample material to be analyzed; said sample excitation apparatus generates said electrical discharge with a duration of less than one millisecond; and said controller structure initiates said gating interval at least thirty microseconds subsequent to application of maximum electric discharge current to said sample material by said excitation apparatus.

23. A method of spectroanalysis comprising the steps of
exciting sample material to be analyzed to spectroemissive levels with excitation apparatus to generate a beam of radiation by triggering said excitation apparatus to generate an electrical discharge with a maximum amplitude of at least ten amperes and of decreasing magnitude after said maximum amplitude for application to sample material to be analyzed;
dispersing said beam of radiation into a spectrum for concurrent application to a plurality of exit ports;
monitoring radiation at each said exit port with channel circuitry corresponding to head said exit port; and
generating a gating interval that commences subsequent to application of maximum energy to said sample material by said excitation apparatus for accumulating data on radiation monitored by said channel circuitry during said gating interval.

24. The method of claim 23 wherein said sample material is excited by application of an electrical discharge with a duration of less than one millisecond to said sample material.

25. The method of claim 24 wherein said gating interval is initiated at least thirty microseconds subsequent to application of maximum energy to said sample material by said electrical discharge and has a duration of less than one millisecond.

* * * * *